United States Patent
Zumbrunnen et al.

(10) Patent No.: US 10,806,626 B2
(45) Date of Patent: Oct. 20, 2020

(54) METHOD AND APPARATUS OF A SELF-MANAGED PORTABLE HYPOTHERMIA SYSTEM

(71) Applicants: Michael Lynn Zumbrunnen, Rochester, MN (US); Laura Marie Zumbrunnen, Rochester, MN (US)

(72) Inventors: Michael Lynn Zumbrunnen, Rochester, MN (US); Laura Marie Zumbrunnen, Rochester, MN (US)

(*) Notice: Subject to any disclaimer, the term of this patent is extended or adjusted under 35 U.S.C. 154(b) by 1243 days.

(21) Appl. No.: 15/004,913

(22) Filed: Jan. 23, 2016

(65) Prior Publication Data
US 2017/0209304 A1    Jul. 27, 2017

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0008* (2013.01); *A61F 2007/0052* (2013.01); *A61F 2007/0063* (2013.01); *A61F 2007/0228* (2013.01); *A61F 2007/0287* (2013.01)

(58) Field of Classification Search
CPC ...... A61F 2007/0008; A61F 2007/0052; A61F 2007/0063; A61F 2007/0228; A61F 2007/0287; A61F 7/0085; A61F 7/02
See application file for complete search history.

(56) References Cited

U.S. PATENT DOCUMENTS

| | | | |
|---|---|---|---|
| 4,382,446 A | 5/1983 | Truelock | |
| 5,755,755 A * | 5/1998 | Panyard | A61F 7/02 607/104 |
| 5,950,234 A | 9/1999 | Leong | |
| 6,030,412 A * | 2/2000 | Klatz | A61F 7/00 607/104 |
| 6,312,453 B1 * | 11/2001 | Stefanile | A61F 7/10 607/108 |
| 8,001,794 B2 | 8/2011 | Windisch | |
| 8,613,762 B2 | 12/2013 | Bledsoe | |
| 8,900,170 B1 | 12/2014 | Elkins | |
| 9,029,736 B2 | 5/2015 | Lavin, Jr. | |
| 9,101,463 B2 | 8/2015 | Stormby | |
| 2004/0158303 A1 * | 8/2004 | Lennox | A61F 7/0085 607/109 |
| 2006/0195168 A1 * | 8/2006 | Dunbar | A61F 7/00 607/108 |
| 2010/0106229 A1 * | 4/2010 | Gammons | A61F 7/0085 607/104 |

(Continued)

*Primary Examiner* — Kaitlyn E Smith
*Assistant Examiner* — Tigist S Demie
(74) *Attorney, Agent, or Firm* — Ojanen Law Office; Karnna Ojanen

(57) ABSTRACT

A non-user assisted, portable, entirely self-managed capable hypothermia device to eliminate hair loss caused by the side effects of certain chemotherapy treatments or to reduce the metabolic rate of ischemic tissue along with the severity of swelling is disclosed. The device consists of a conformal cap system, a thermally conductive liquid located between the body part to be cooled and the cap system, thermal transfer fluids, phase change materials, thermally insulated cooler, physical measuring devices, mechanical and electrical components, a 'smart' user interface device, a battery, and an uninterruptible power controller.

10 Claims, 6 Drawing Sheets

(56) References Cited

U.S. PATENT DOCUMENTS

| | | |
|---|---|---|
| 2013/0138185 A1 | 5/2013 | Paxman et al. |
| 2013/0317578 A1* | 11/2013 | Diller ................. A61B 5/01 607/104 |
| 2015/0057656 A1* | 2/2015 | Gupta ............. A61B 18/1492 606/41 |
| 2017/0239082 A1 | 8/2017 | Unver et al. |
| 2017/0239083 A1 | 8/2017 | Unver et al. |
| 2017/0296379 A1 | 10/2017 | Paxman et al. |
| 2019/0240192 A1 | 8/2019 | Georgopoulos et al. |

* cited by examiner

METHOD AND APPARATUS OF A SELF-MANAGED PORTABLE HYPOTHERMIA SYSTEM

CROSS REFERENCE TO RELATED APPLICATIONS

This application is based on and claims priority and benefit of Provisional U.S. Patent Applications No. 62/112,110 filed Feb. 4, 2015; Application No. 62/112,117 filed Feb. 4, 2015; Application No. 62/112,121 filed Feb. 4, 2015, and their entire contents of which are incorporated herein by reference.

TECHNICAL FIELD

This invention relates in general to methods and systems to eliminate hair loss caused by the side effects of certain chemotherapy treatments and to reduce the metabolic rate of ischemic tissue along with the severity of swelling. Still more particularly, the present invention relates to methods and systems to enable the user to self-manage its entire operation without assistance.

BACKGROUND OF THE INVENTION

Therapeutic hypothermic treatments can reduce the distressing side effect of alopecia caused by chemotherapy treatment by cooling the scalp to below 19° C. during the chemotherapy session and for a brief time before and after the session. No other cooling times are required. The cold scalp temperature serves two purposes. One purpose is to reduce the circulation of blood flowing to the hair follicle cells so less chemo reaches the hair follicle cells. The second serves to decrease the uptake of the chemo drugs by the hair follicle cells preventing the chemo from getting inside the hair cells and killing them. For these reasons, scalp cooling should only be used on solid tumors not located in the head region.

Hypothermia treatment for ischemic injuries has been known for years and is generally accepted to effectively reduce the metabolic rate of ischemic tissue and the severity of swelling. Sprains and muscle pulls are commonly treated with ice packs to provide the hypothermia. The simplicity of ice pack treatment allows it to be used nearly at the same time of the injury which, in turn, has contributed to its effectiveness.

Given the known range of head sizes and head power, effective hypothermia treatment of the head region whether it be for treatment of alopecia or for ischemic injury requires overcoming a large thermal resistance associated with the thermal properties of the hair which can vary significantly from person-to-person due to, for example, amount and thickness. People skilled-in-the-art of heat transfer recognize hypothermia systems must provide a sufficiently cold surface in contact with the hair so that a large temperature difference between the cold surface and scalp will overcome the hair thermal resistance. For example, suitable cold surfaces may be achieved by pumping cold antifreeze fluids through conduits in a head surrounding cap; by cold packs placed around the head pre-cooled by dry ice or industrial grade freezers set at less than −30° C.; by cold packs made cold by endothermic chemical reactions; by cold caps made cold by piezoelectric effects; by cold gases pre-cooled by refrigeration systems or Joule-Thomson effects; or by other means.

People skilled-in-the-art of health delivery recognize the efficacy of a treatment correlates with its simplicity and ease-of-use whether implemented by trained personnel or by the user. Effective hypothermia treatment of the head region also requires the user or support personnel to be trained to fully comply with operational instructions of the device.

An inherent difficulty exists with cold packs pre-cooled by dry ice or refrigeration systems because they do not have enough thermal capacity to allow for a single cap to be used throughout the duration of cooling. Thus, fresh cold caps must replace the warmed caps approximately every 20-30 minutes. The process of removing and replacing caps increases the likelihood of poor results and is especially very difficult to do without assistance while connected to chemotherapy tubes.

Similarly, foldable cold caps formed in-situ to the user's head by wrapping, connecting tabs, filling air bladders, or by splicing multiple pieces together in a manner to improve fit require assistance to the user to don properly.

Effective hypothermia treatment of the head region also requires the device to be ready and available when needed. Cooling devices owned and maintained by the healthcare facility may not necessarily be available due to scheduling conflicts or simply not geographically near the user.

Complex hypothermia head cooling solutions such as those using refrigeration systems or multi-faceted head wraps tend to required on-site trained personnel to implement which in itself inhibits availability due to healthcare providers not wanting the capital equipment to own, store, and maintain besides the added responsibility and liability to have a trained staff for a treatment that is primarily cosmetic. These complex cooling devices tend to be more costly and may result in fewer users available to benefit from the treatment. Also, recent studies regarding therapeutic hypothermia for concussions indicate cooling may reduce primary and secondary injuries to the brain and is more effective if administered as soon as possible after an injury thus scheduling conflicts or geographic constraints will adversely impact the efficacy of this treatment.

Refrigeration systems, large equipment, sophisticated operating panels, manuals with medical jargon, and odd fluids with special handling requirements appear unwieldy and complicated to most users to self-manage, especially at a time of duress. Effective hypothermia treatment of the head region to be self-managed by the user require self-evident familiarity of equipment, its components, and controls such that operational anxiety and mistakes can be minimized. Also, self-managed devices require in real time "on-demand" services that are not available to those devices dependent on trained personnel as the middle man between the device and the user.

Effective hypothermia treatment of the head region requires certain physical data measurements such as temperature or EEG waves and machine operating conditions such as fluid flow rates or voltages be collected so that user compliance can be verified and the equipment can be improved.

Systems requiring industrial refrigerators or integrated refrigeration units tend to be expensive for medical facilities to own, store, and maintain. Although costs may be amortized across multiple users, an inherent cost exists compared to those devices that use commercially available materials, fluids, self-managed, and maintained. Effective low cost devices for hypothermia treatment of the head region requires costs to be low all aspects of operation whether it be capital, operating, maintaining, storing, user, or medical facility and personnel costs.

Large stationary or multi-user refrigeration systems reside at a clinic therefore cool down cannot start at home or in transit to the clinic. Stationary systems require the user to be tethered to the system from beginning to end and with scalp cooling for preventing hair loss, the beginning of use starts before treatment and the end of use can be several hours after the chemotherapy treatment has ended. For restroom visits, the user must temporary stop usage and hope the warm-up was not too severe to cause hair loss. Equally disconcerting for the preventing hair loss application, is that tethered to a stationary or multi-user system means the user cannot attend other appointments during the post treatment phase. Thus, mobile systems with uninterruptible power sources combined with self-managed controls are required for effective hypothermia systems to be used "on-the-go" from beginning to end of use.

SUMMARY OF THE INVENTION

Accordingly, the primary object of the present invention is to overcome the shortcomings of the prior art systems by providing a hypothermia system that can be fully implemented solely by the person using the invention, is readily available, low cost, prevents hair loss during chemotherapy, or can provide rapid application of cooling to positively affect multiple aspects of brain trauma, and includes
  a flexible and conformal cap system with at least one contiguous fluid conduit from an inlet connector to an outlet connector formed to substantially encapsulate the body part to be cooled, has one or more physical measuring devices, has covering said conduit on surfaces away from said body part a stretchable insulating outer shell with chinstrap, and a secondary stretchable insulating material around said outer shell to circumferentially squeeze the conduits to close proximity to that to be cooled;
  a thermally conductive biocompatible liquid substantially displacing the air surrounding the user's hair strands and filling the gaps between the body part to be cooled and the conduit outer surfaces forming the interior of the cap;
  a 'smart' user interface device with logic commands to provide self-managed ease-of-use, user instructions, system control and monitoring, where said self-managed ease-of-use includes user's ability to infinitely control within predetermined bounds the rate of cool down, where said control includes algorithms to evaluate physical measuring devices and alert user for intervention, if warranted, or automatically make system adjustments;
  a thermally insulated cooler system with a tank, a mechanical compartment, an electrical compartment, and plumbing components, with said tank holding a thermal transfer fluid and phase change material, said mechanical compartment having one or more sensors and a pump to circulate the transfer fluid, said electrical compartment having electrical components to control and power the system including an uninterruptible power controller to automatically switch between battery power and external power.

Another object of the present invention is to provide a generally accepted user interface to control the system.

A further object of the present invention to provide a single cap for use throughout the entire treatment.

Yet another object of the present invention is for the device to be fully functional while in transit or away from the treatment center. This could be for example restroom visits, other appointments, walking to/from one's car, traveling in a car, or simply finishing the cooling phase at home.

BRIEF DESCRIPTION OF THE DRAWINGS

The invention will be described in greater detail with reference to the accompanying drawings which represent a preferred embodiment thereof, wherein.

DETAILED DESCRIPTION

Figure 1:
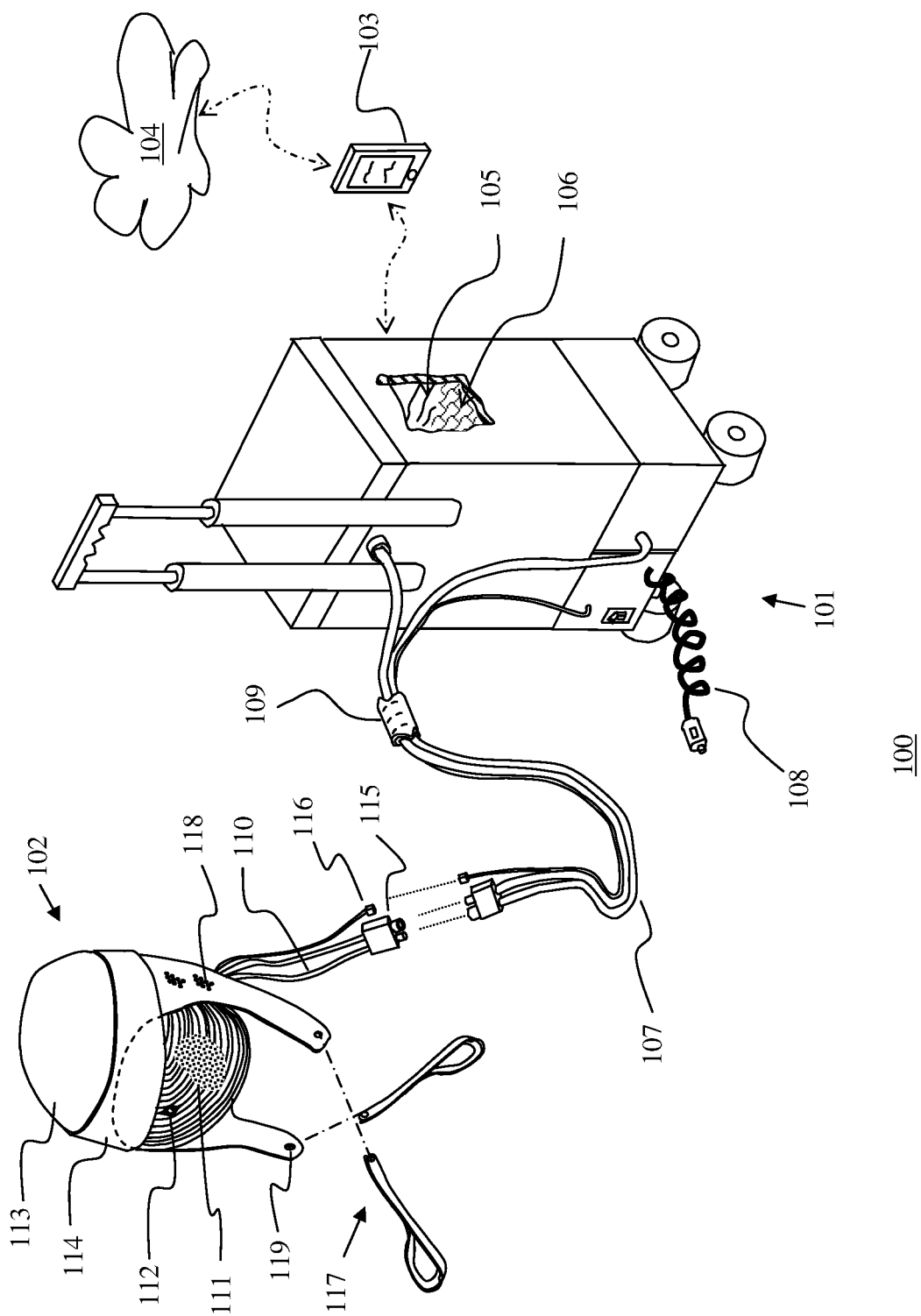
FIG. 1 is an isometric view of a preferred embodiment of the self-managed, mobile, hypothermia system.

With reference to FIG. 1, a self-managed portable hypothermia system 100, according to an embodiment of the present invention, includes a portable cooler system 101, a flexible and conformal cap system 102 that is worn by a user, a smart mobile device 103 which is wirelessly connected to the said cooler system and remote data storage 104 as shown by the dashed lines is illustrated. The said cooler system comprises of a thermally insulated, leak proof cooler for containing a thermal transfer fluid 105 and phase change material 106; a telescoping handle system with casters to aid system mobility; an electrical control box; a mechanical control box; electrical and plumbing conduits 107 linking the cooler system with the said cap system; and an electrical connection 108 to a 12 volt source such as an external battery or motor vehicle or in combination with a AC/DC adapter to typical AC power such as 120 V wall sockets. The plumbing conduits 107 are encapsulated by a vapor barrier and thermal insulation 109 (shown partially) to eliminate condensation and minimize heat gain respectively.

The purpose of the phase change material 106 is for exploiting its high energy storage capacity (i.e., latent heat of fusion) at a temperature sufficiently below the desired head temperature so that as the heat transfer fluid 105 is pumped through the cap system 102 enough energy can be removed from the head and transferred to the phase change material.

The purpose of the casters and telescoping handle is to aid in the mobility object of the invention. The entire system 100 can be operated and transported by a single person.

The flexible and conformal cap system 102 consists of a single continuous high thermal conductivity thin wall conformal conduit 110; a high thermal conductivity liquid agent 111 (partially shown); one or more physical measuring devices 112 for temperature or brain activity measurements, an outer shell 113 to thermally insulate the cap and assist in maintaining the cap snug against the head; a secondary flexible and conformal head band 114; drip-less fluid connectors 115; a connector 116 for sensors; and supplemental cap inverse suspenders 117. The head band 114 improves heat transfer and sensor contact by cap circumferential squeeze. A similarly shaped head band resides under 114

(not shown) but angled downward to only cover the skin can be used to prohibit seepage of any liquid agents 111 used between the head and cap. Contributing to the ease-of-use and self-managed objects of this invention are the preferred use of gender specific plumbing connectors for direction of fluid flow and a standard everyday and familiar phone jack connector for the sensor wire connections. Said connectors 115 have their mating fluid and sensor connectors located on cooler system 101. The user cannot connect either type together incorrectly. The design of the shape of the cap system 102 enables easy user recognition of its front and back such that it is easy for the user to orient and put on.

The liquid agent 111 is applied by the user across the entire inside surface area of the cap, copiously throughout the user's hair (not shown) that contacts the cap, and the grooves located between adjacent conduits. In the preferred embodiment, the liquid agent is a water based gel for high conductivity, ease of application, cleaning, and may optionally contain ingredients to preserve the skin or hair of the contacting body part.

The desired scalp temperature is achieved by the preferred embodiment of the hypothermia system for eliminating or reducing hair loss because of a paradigm shift of how to overcome the total thermal resistance from the head surface to the liquid phase of the phase change material. Key to this paradigm shift is use of the said gel 111 which dramatically reduces the thermal resistance of the hair to magnitudes that enable trade-offs with other thermal resistance elements in the overall heat transfer path. In essence, the gel enables other elements of the system to be simple and common such as water for the transfer fluid 105 and ice 106 for the phase change material which makes a low cost, portable, self-managed hypothermia system possible since water and ice are readily available for the user whether be at a user's home or at a local convenient store. Furthermore, the ice and water can co-mingle in the preferred embodiment which as a result eliminates all thermal resistances associated with transferring heat through whatever packaging is implemented for separating the phase change material from the transfer fluid. In the absence of gel, circulating ice water will not achieve a cold enough scalp temperature to save one's hair while undergoing chemotherapy treatments for cancer.

Although numerous methods may appear adequate to wet the hair with gel, it is important to replace the air between the hair strands with gel, have the hair/gel composite thin, and lay flat against the scalp. In the preferred embodiment for eliminating or reducing hair loss, the method for the user to apply said water based gel copiously to the user's hair is to

- use a comb to part back of head near midline, apply gel to both sides of said part;
- make a similar part about ½-1" to the right of first part, and apply gel to both sides again;
- continue making parts about 1" to the right applying gel to both sides until ear is reached;
- repeat on the left side of center back part until left ear is reached;
- make a part down front center, apply gel to both sides;
- repeat part to right of center about ½-1" until meet where gel is on right side;
- do to the left of center part;
- take wide tooth comb and comb through hair to shoulder length;
- while combing through, distribute hair evenly and flatten to scalp.

Also in the preferred embodiment, the said water based gel is applied copiously all over inside of cap by the user using their fingers to spread gel evenly throughout the inside of the cap, filling the grooves present between adjacent conduits.

During operation of the hypothermia system of this invention, heat is extracted from the head, through the gelled hair, to the pumped transfer fluid which returns to the cooler where the ice absorbs the energy contained in the fluid. The energy is transferred at first by warming the ice to its phase change temperature and then by changing its phase from solid to liquid. The newly formed liquid becomes additional transfer fluid available for circulation.

This invention does not preclude other material selections for the transfer fluid and phase change material. Those skilled-in-the-art of heat transfer and material science may trade-off design parameters in a manner that enables, for example, a saline solution to be used as the transfer fluid and phase change material at the expense of ease-of-use and availability. Alternatively, one may use an anti-freeze for the transfer fluid and an engineered phase change material that are kept separated by a membrane or other packaging means. Although alternative methods may achieve scalp cooling it will be at the expense of one or more objects of this invention thereby impacting its acceptance by a user, clinic, or healthcare provider.

The cooler system 101 holds sufficient transfer fluid and phase change material to maintain cooling for the duration of most treatments. An additional charge of phase change material is added to the cooler by the user for especially long treatments (e.g., 10 hours) or for embodiments having coolers with less than 15 liter capacity. The use of water and ice simplifies the user's skills required to add an additional charge. The cooler is sufficiently insulated such that the transfer fluid it holds is maintained near its phase change temperature throughout its duration of use. In the preferred embodiment, 10 pounds of ice and 1 gallon of water provide ample cooling duration for the user.

The outer shell 113 and head band 114 are of insulating and light weight material such as neoprene so user comfort is maintained throughout duration of use. The outer shell is perforated at certain locations 118 to aid in the ability to hear but not compromise on strength of the material. The cap worn over one's head has protective covering of the ears to prohibit local over cooling and has provisions for holding eye wear without impeding the performance of the device. Graspable regions around the said outer shell aid installation and facilitate a tight fit to the head and at certain locations 119 can attached to the aforementioned inverse suspenders 117 for additional assurance of a snug fit. If suspenders 117 are not used, the locations 119 can attach to each other under the user's chin. There are provisions in the outer cap 113 for circumferential elastic ribbons to further improve the snug fit and optionally worn for fashion comfort. The outer shell can be oversized beyond the cooling portion of the head for insulating bare skin regions. An even outer portion (not shown) beyond 113 can be worn for fashion comfort and even added insulation. Three to five conformal caps 102 of various sizes are required to service a broad range of head sizes.

Figure 2:
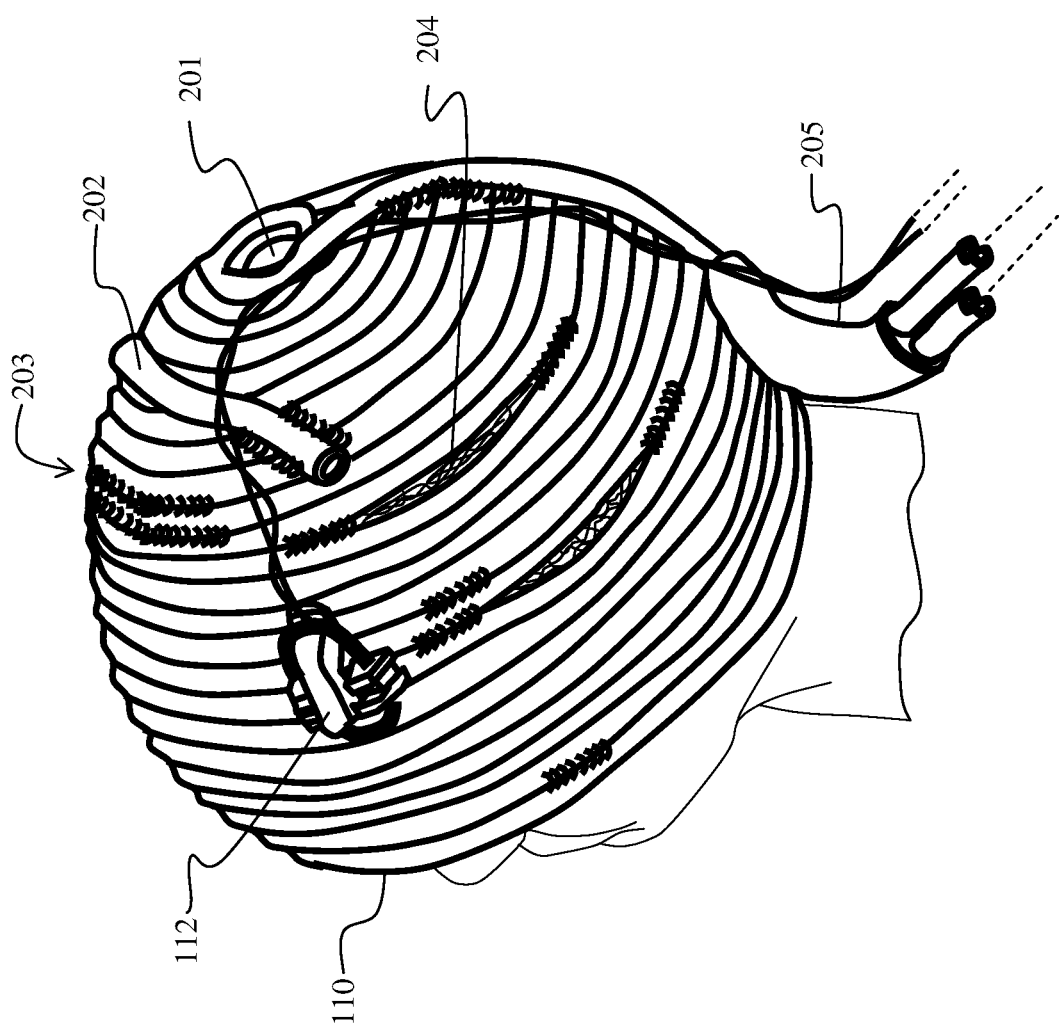
FIG. 2 is an isometric rear left view of a user wearing a flexible and conformal cap and for depiction purposes is shown without its outer shell or supplementary headbands.

With reference to FIG. 2, an isometric rear left view of a user wearing a flexible and conformal cap is depicted and for delineation purposes is shown without its outer shell 113 or supplementary headbands 114. An opening 201 at the top of the cap enables air to escape that otherwise would have been trapped between the head and cap tubes while putting on the cap due to the snug fit of the cap to the head. Large amounts of residual air will resist compression and counteract the desired cap fit. For the preferred embodiment with a water based gel, a cap is made from about a 10 meters of 5/16" diameter, 1/16" wall thickness silicone rubber tubing. The silicone material allows for cap flexibility, durability, and thermal conductance. The conduit 110 cross section for fluid flow is reduced in area after securing the cap to the head due to its conformal properties thereby improving its laminar heat transfer capability. The material durometer is significantly high so that pinching cannot occur. The tube is wrapped in a continuous spiral having contiguous windings to match typical head shapes and kept together with silicone rubber adhesive 203 (partially shown). Said adhesive is applied as a fillet at each conduit-to-conduit contact across the entire outer surface of the cap except if certain compliancy locations 204 are implemented. The fillets of adhesive seal the cap water tight thereby entrapping the said liquid agent between the scalp and cap interior. Additionally, the adhesive improves the effectiveness of the conduits heat transfer by augmenting the conduction path to the far side conduit wetted surfaces. One or more physical measuring devices 112 are attached to the conduits by adhesive. Select conduit-to-conduit contact locations may be absent of adhesive to enhance cap conformity. To assist in conforming the cap to the user's head, additional material 202 is selectively located around the top portions of the cap so reactive forces created by securing the outer shell 113 are applied to the cap at locations ensuring a consistent fit across the surface area of the head. The said compliancy locations 204 minimize conduit counter forces and allows for the conduits affected by the additional material to move closer to a surface below.

The conduits 110 are routed inside a larger anti-pinching conduit 205 having a portion of length overlapping several circumferentially wrapped conduits and another portion at least several inches beyond the largest opening of the cap. The anti-pinching conduit reinforces the cantilevered portion of the conduits so than bending or twisting of the cap does not cause the fluid channel to pinch shut.

Figure 3:
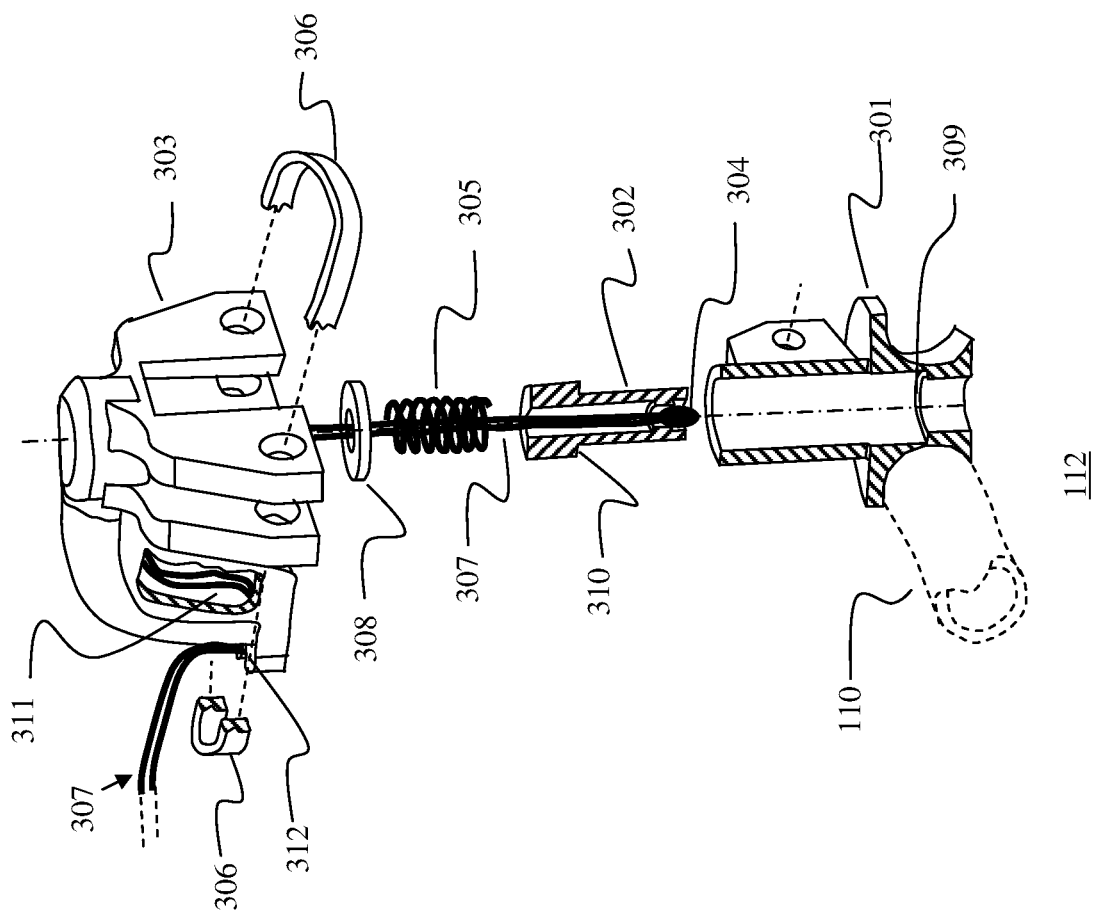
FIG. 3 is an exploded isometric cross-sectional view of a physical measuring device with some components cross-sectioned.

With reference to FIG. 3, the physical measuring device 112 comprises of a stationary part 301 that is fixed between adjacent conduits 110 (one not shown) and not attached to the component to be measured such as a person's head, a movable part 302 that can travel along its major axis within the said stationary part with one end of the movable part able to protrude from the stationary part and make contact or be in close proximity to the component to be measured such as the scalp of one's head, a restraining part 303 that attaches to the stationary part on the side opposite the component to be measured and retains the movable part within the stationary part, one or more sensors 304 such as a thermistor or EEG element with its sensing portion at the protruding end of the movable part and its electrical wires 307 exiting out near or at its other end, a spacer 308, a spring 305 located between the cap and movable part end having wires exiting thereby applying force on the movable part such that contact or close proximity to the component occurs, a cable tie 306 that locks the restraining part 303 onto the stationary part 301 and also inhibits external forces on the wires to cause any unwanted sensor movement. The stationary part 301 is typically held in place in the cap by silicone adhesive 203 whereas the movable part, sensor, washer, and spring are mechanically held in place by the restraining part 303 and cable tie 306.

The stationary part 301 is made of insulating material such as plastic and is hollow or of sparse interior material composition thereby effectively reducing its thermal conductivity. The inner chamber of the stationary part is for containing one or more movable parts and is sized to permit the movable part installation from the side opposite that of the component to be measured and prohibit the movable part from protruding beyond a prescribed amount by stop feature 309. The stationary part surface in close proximity to the body part can be contoured to match the surface contour of the head.

The movable part 302 is also made of insulating material such as plastic and is hollow or of sparse interior material composition thereby effectively reducing its thermal conductivity. The stationary and movable parts can be of different material types. The movable part 302 has a hollow core spanning its entire length so that electrical wires 307 can be routed from the sensor through the core of a spring 305 and spacer 308. The spring 305 is made of non-corrosive material such as stainless steel and exerts a force on the movable part. The spacer 308 length can be modified to tune spring force and travel. The minimum and maximum travel of the movable part is determined by a composite of spring length, length of said internal cavity, movable part length, and locations of the stop features 309 and 310. Typical movable part travel is normal to the component to be measured with maximum inward travel yielding the sensor flush with the bottom surface of the stationary part and maximum protrusion of 3/16". For certain cases, the travel may not be normal to the component to be measured. Non-normal travel may be desirable for hard to reach areas or if the sensor geometry is asymmetric. In the preferred embodiment of the invention, the sensor is slightly recessed into the movable part and secured with thermal conducting epoxy.

The measurement by the sensor 304 is minimally impacted by the cold transfer fluid 105 traveling through the conduits 110 because of a high thermal resistance path existing between the head and transfer fluid on the one side and on the other side, the small physical size of the measuring device components, and the low thermal conductivity, and sparse internal structure of the stationary part 301 and the movable part 302, and a gap between the movable and stationary parts. In the preferred embodiment, the movable part is 1/8" diameter but its cross section is not required to be circular.

The retention part 303 has a relatively large internal cavity 311 for the sensor wires 307 to occupy as they move freely as the movable part travels up or down. The travel up or down occurs predominately whenever the user installs the cap on their head and travels slightly due to thermal contractions and expansions of the materials. The sensor wires are locked at one end of the cover by the cable tie 306 wedging the sensor wires against retention tab 312 thereby creating strain relief for the sensor wires.

The physical measuring device 112 is replaceable and reusable. In some cases, it may be desirable for movable part not to be installed thereby leaving its associated cavity in the stationary part available for other uses such as viewing, installing a different sensor, or as an access port to the head.

Figure 4:
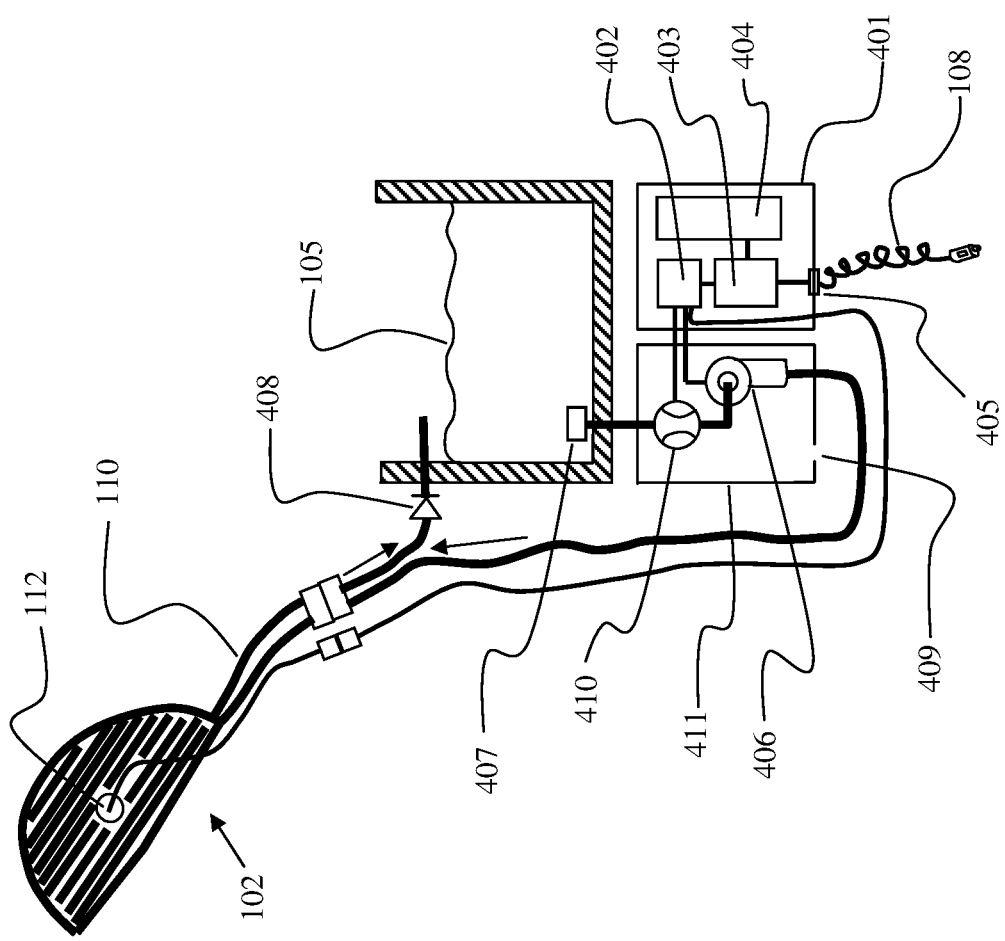
FIG. 4 is a combined fluid flow diagram and electrical wiring schematic of the hypothermia system.

With reference to FIGS. 1 and 4, an electrical control box 401 contains an on-board microprocessor 402; an uninterruptible power controller 403, a battery 404, and an on/off power switch 405. The microprocessor 402 receives electrical data signals from the physical measuring device 112, flow meter 410, and via wireless communication master control data from the smart mobile device 103. The microprocessor manipulates the said data and outputs control data to the pump 406 located in the mechanical control box 411 and to the master controller 103. Not shown are the ancillary electrical components to reduce electrical noise effects on the sensor measurements and a voltage regulator to adjust incoming voltage to levels suitable for the microelectronics.

For low cost and proven reliability, the preferred microprocessor embodiment employs analog signal processing for sensor measurement with digital pulse-width-modulation for variable voltage output to adjust pump flow rate in order to raise or lower the temperature of the head. The uninterruptible power controller 403 continuously monitors the supply power from the external power source 108 and on-board battery 404. The power controller 403 automatically switches between power sources if one is deemed unacceptable for use. Re-charging the battery is also controlled by the uninterruptible power controller.

In the preferred embodiment, the pump 406 is of positive displacement type thereby able to generate sufficient pressure to force the transfer fluid though the tubes, disconnects, valves, and other plumbing components in the fluid path. A strainer 407 is located in the suction path upstream of the pump. The strainer prohibits any small particles to be introduced into the pump and is especially useful for those cases where the phase change material co-mingles with the transfer fluid. A check valve 408 is downstream of the output from cap 102 and is oriented to prohibit the cap to drain for those occurrences when the pump is off thereby trapping the high thermal capacity transfer fluid in the conduits to absorb heat from the head while the fluid is stationary. The check valve enables the microcontroller to sequence the pump on and off rather than run continuously. In the preferred embodiment, the pump runs at a 50% duty cycle. The non-continuous pump operation allows for longer battery life and contributes to achieving the mobility object of the invention. The pump may run at full power continuously if the microprocessor evaluation of the system data deems it to be necessary to meet the hypothermia objectives set by the system and user. One or more drain holes 409 are located in the mechanical box 411 in case any leakage of the plumbing hardware may occur. The electrical box 401 is isolated from the mechanical box except for a small sealed wiring conduit.

Figure 5:
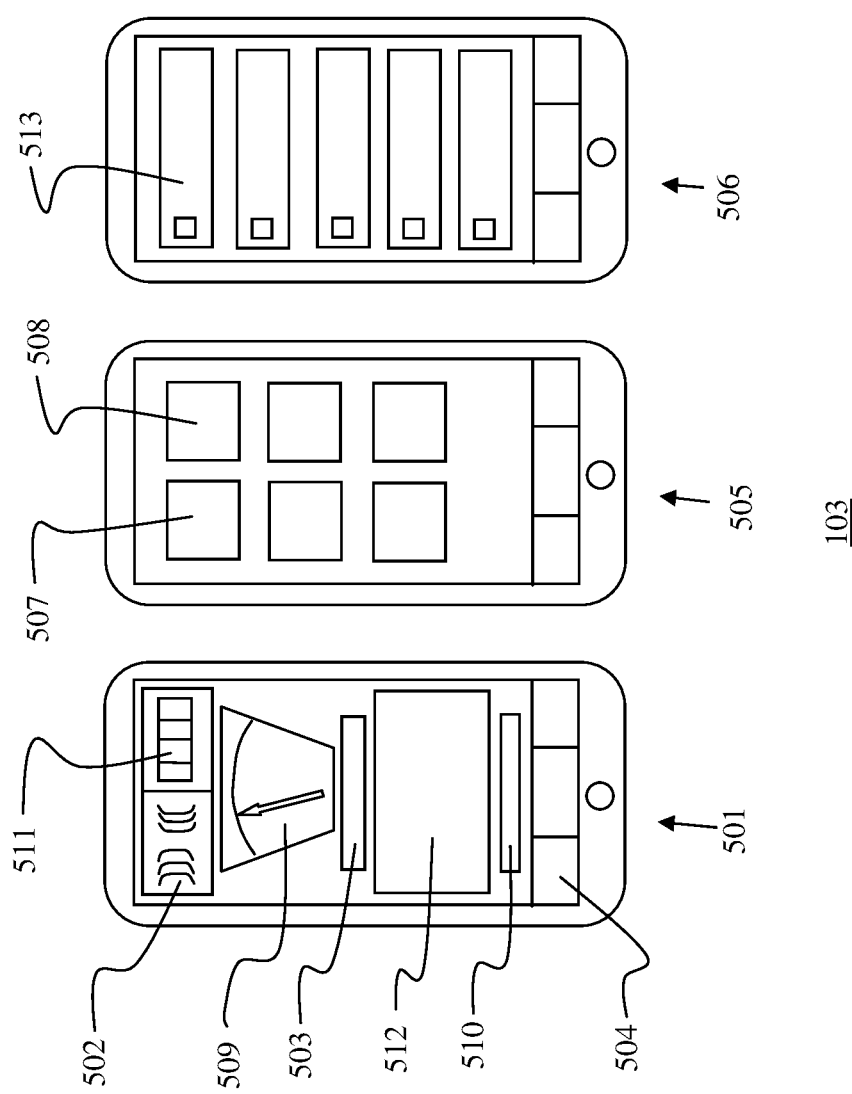
FIG. 5 is a pictorial of three screen shots of a user's smart mobile device for monitoring and controlling the hypothermia system.

With reference to FIGS. 1 and 5, the smart mobile device 103 is the master controller of the hypothermia system. Look and feel of its operation follows present de-facto smart phone applications in regard to input, feedback, responsiveness, pop-up alerts, and pop-up notices. Its familiarity reduces user anxiety that may exist from seemingly complicated and high tech instrumentation evident on other devices found in the healthcare industry. The smart phone device has powerful on-board computing capabilities, wireless communication components, and a high resolution display all of which are leveraged by this invention without inheriting their costs. Similarly, the smart mobile device application can automatically and securely connect to an on-line database 104 for real time updates to certain parameters of the application software. Significant revisions can occur in less that three days world-wide in today's standards. Hence, the implementation of a user's own smart mobile device contributes to satisfying the ease-of-use, low cost, and availability objects of this invention.

To operate, the self-managed portable cooler system 101 and smart mobile device 103 must be powered-on. Wireless communication with one another must occur at the beginning of operation but not necessarily throughout the entire duration of treatment. Communication occurs by the user opening the application software on the mobile device, pushing the connect button 502 on the home screen 501 then enters a unique device ID provided by the manufacturer in the application window 503. The software automatically pairs the mobile device to the hypothermia system and locks-out all other devices. The system operation cannot proceed unless connected and the user agrees to manufacturer terms and conditions which are presented to the user automatically before the start of each session. Also included on the session screen 501 are the power level indicator 511, sensor performance gauge 509, status text screen 512, tab selection buttons 504, and user customization input slider 510. The aforementioned screen windows are not necessarily visible to the user at all times.

Once connected and terms are agreed to, the user can choose to continue with the session or move to the information screen 505 or tools screen 506 via the tab selection buttons 504. Instructional videos 507 and manuals 508 for how to, for example, prepare the cooler with transfer fluid and phase change material; how to put-on the cap; how to operate the application; how to service the system; how to clean the system; how to run on battery mode; and, how to interpret alarms and warnings. All are available at any time the user selects the information screen. The tools screen includes, for example, user selection 513 to customer service contacts, evaluation forms, frequently asked questions, and instructions for the system to drain itself once the hypothermia treatment has ended. The user can choose at anytime during the hypothermia treatment to text, email, or phone customer service without compromising the function of the system. Similarly, the user can open other applications found on the smart mobile device such as videos, web browsing, social networks, etc. while the hypothermia application continues to run in the background.

For the hair preservation preferred embodiment of the hypothermia system, the session screen 501 progressively illustrates six phases of operation. The six phases are cap fit, cool down, maintain, treatment, post-treatment, and conclude. The cap fit phase polls the sensors in the cap and determines if the fit of the cap is adequate to proceed to the next phase. The algorithm examines left-right, front-back, or other sensor comparisons to determine if measured variations are within expectations for the application. Once the cap fit phase ends, the user enters the cool down phase. Cold transfer fluid starts flowing through the conduits in the cap at a relatively slow flow rate. A controlled rate of cool down is tailored to the user to rates by their own choosing within certain functional bounds of the system. Twenty to thirty minutes is chosen by most users to comfortably achieve a scalp temperature below 19° C. The customization slider 510 permits the user to adjust the rate of cool down. Once the temperature is achieved, then the maintain phase begins. This phase maintains the temperature while the user is waiting for the treatment to begin. Once the treatment begins, the treatment phase begins. Post-treatment phase maintains the scalp temperature for a set time period based on the chemo regimen. This phase could last upwards of 5 hours. Due to the on-board battery 404 and uninterruptible power supply 403, the user can freely choose to be mobile and travel at-will without compromising functionality of the hypothermia system.

Figure 6:
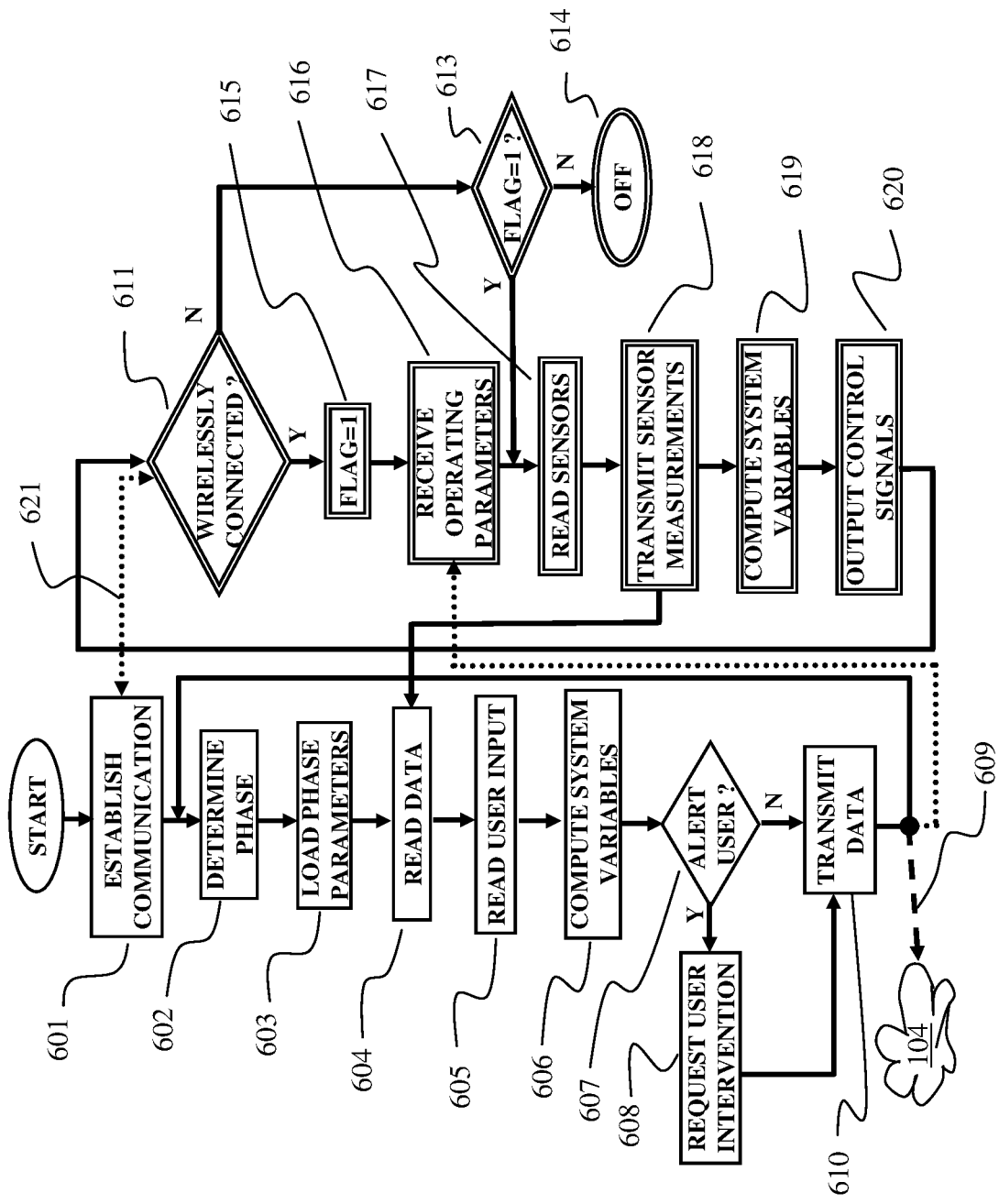
FIG. 6 is a logic flow chart of the embodiment shown in FIG. 1.

With reference to FIGS. 1, 4, 5, and 6, in many respects, the success of contributing to the self-managed object of the invention exists because of under-the-covers automatic software managed control of the hypothermia system embedded in the application software 103 and microprocessor 402. Once the button 502 is pushed, the application attempts to establish wireless communication 601 with the microprocessor decision block 611. Communicating and pairing activities occur continuously while both devices are powered and a successful communication pairing sets a flag 615 to one (i.e., logical TRUE). Single line bordered symbols represent function located in the smart user interface device whereas double line bordered symbols represent function located in the microprocessor. Those skilled-in-the-art of programming may choose different allocations of code blocks (single/double line) but FIG. 6 represents the preferred embodiment to satisfy several objects of the invention.

The said phases of operation have different operating parameters and block 602 determines the active phase and loads its corresponding operating parameters 603 into appropriate variables such as set points, times, limits, alarm values, etc. The hardware sensors 617 read from the microcontroller and transmitted 618 for the mobile device to read 604. Coupled with optional user input values 605, newly acquired information is supplied to an algorithm 606 for system evaluation. In the cool down phase, the algorithm provides a controlled rate of cool down thereby enabling the user to acclimate to the colder temperature. The user may choose to change the rate of cool down and provide a rate adjustment as a user customization value 605.

Decision block 607 has algorithms customized to each phase. For instance, a relatively high temperature value in the cap fit phase is desirable where a high value in treatment phase is an indication of a potential fault. Acceptable operating parameters are transmitted 610 wirelessly (dotted line) to the system hardware code 616 where default values are over written.

The user may be notified for an intervention 608 if decision 607 determines a value is unacceptable. One example is if the user forgets to add transfer fluid into the system or forgets to connect the drip-less fluid connects 115 together. For this example, a flow meter would measure no flow and the algorithm would determine a fault condition and notify the user to add fluid. Another example is if the user forgets to connect the sensor connector 116 then erroneous measurements would be noticed by the software and intervention then requested.

Sensor readings 617 are modified, compared to control parameter values 619, and with algorithm 606 control levels are adjusted to bring the system closer to desired levels. Those skilled-in-the-art of control theory can apply various control procedures such as proportional-integral-derivative algorithms to adjust pump speeds 620 to achieve a scalp temperature. In essence, the code runs continuously in a loop reading sensors 617, transmits 618 to mobile device, combines user input 604, set hardware controls 619, and does error checking 606. A fault or error that is controlled automatically (i.e., user intervention does not occur) is, for example, if 606 determines 604 is unsafe (i.e., temperature too cold), then control signal 620 sends shuts off signals the pump.

Once flag 615 is set as determined by decision block 613, the hardware can operate to most recently updated control parameter values in the absence of wireless communication 621. For this case, however, user inputs 605 are not available to the hardware until communication is re-established. If the flag is never set or if the control signals stipulate, the system is turned off at block 614.

The smart mobile device code continuously monitors the system operation. It can, for example, determine if the cap is put on correctly by polling and examining sensors in the cap. It can discern if any sensors are not behaving correctly and either interrupt the user to fix or remove from the control algorithms. It can turn the system off automatically once the appropriate amount of time for a prescribed treatment has elapsed. It can discern if the battery power becomes too low for proper operation and interrupt the user for attention to switch over to wall power.

Periodically, the smart mobile device code transmits data via a communication link 609 to be retained at the remote server 104. Sensor data, control parameters, and user information are part of the data retention package and optionally can be shown to the user at any time. All data is password protected and secured to prevailing government guidelines.

In essence, the user of the hypothermia system of this invention requires no assistance to put on, operate, take-off, or maintain whilst achieving all of the aforementioned objects of the invention.

We claim:

1. A hypothermia system to cool a body part, comprising:
(a) a thermal transfer fluid;
(b) a conformal cap system through which the thermal transfer fluid circulates, the conformal cap system further comprising:
a continuous conduit having a plurality of windings to substantially encapsulate the body part, the conduit having an inlet connector and an outlet connector;
at least one physical measuring device with a sensor wire, the physical measuring device attached to the conduit, the at least one physical measuring device comprising:
a movable part of insulating material having a major axis and a hollow interior;
at least one sensor with at least one connected sensor wire, the at least one sensor situated in the interior of the movable part;
a stationary part of insulating material having a hollow interior in which the movable part is situated and can travel along its major axis;
a restraining part attached to the stationary part at an end opposite the body part to retain the movable part within the stationary part;
a mechanical loading part situated between the restraining part and the movable part, the mechanical loading part to apply force on the movable part to place the at least one sensor in close proximity or in contact with the body part;
an outer shell having a strap, the outer shell covering the conduit snug against the body part;
a secondary material surrounding the outer shell to circumferentially squeeze the conduit to the body part to be cooled;
(c) a thermally conductive biocompatible liquid copiously applied to the body part and to an inside surface and grooves between adjacent windings of the continuous conduit toward the body part to displace air;
(d) a thermally insulated cooler system connected to the conformal cap system, the thermally insulated cooler system further comprising:
a tank for storing the thermal transfer fluid and a phase change material, the tank connected to the inlet connector and outlet connector of the conformal cap system;
a mechanical control box connected to the tank and having at least a flow meter and a pump;
an electrical control box connected to at least the mechanical control box and the at least one sensor wire, the electrical control box comprising a microprocessor, a power controller, a power source, a switch;
at least one plumbing component comprising a check valve between the conformal cap system and the tank to prohibit the thermal transfer fluid from draining out of the conformal cap system when the pump is not operating; and (e) a smart user device connected to the electrical control box, the smart user device further comprising an interface and internal logic by which a user can monitor and control circulation of the thermal transfer fluid through the continuous conduit based on output from the at least one physical measuring device and output from the electrical control box.

2. The hypothermia system according to claim 1, wherein the movable part can travel along its major axes at an angle normal or oblique to the body part.

3. The hypothermia system according to claim 1, wherein the restraining part has provisions to inhibit the at least one connected sensor wire from movement by downstream forces but can move freely as the movable part travels.

4. The hypothermia system according to claim 1, wherein the movable part is not installed in the hollow interior of the stationary part whereby the hollow interior of the stationary part is available for other uses such as viewing or as an access port to the body part.

5. A hypothermia system according to claim 1, wherein the internal logic of the smart user device further comprises control and system monitoring logic to analyze, verify, validate system usage conditions, and logic to transfer at least one or more of the following: data from the at least one physical measuring device, control parameters, user information, system usage conditions to an off-system data storage.

6. A hypothermia system according to claim 1, wherein the thermal transfer fluid and the phase change material are water and ice, respectively, and can co-mingle in the tank.

7. The hypothermia system according to claim 1, wherein the continuous conduit has a thin thermally-conductive wall and conformal characteristics whereby a cross sectional area of the continuous conduit is reduced by forces securing the cap system to the body part thereby improving laminar heat transfer capability of the continuous conduit.

8. The hypothermia system according to claim 1, wherein the conformal cap system further comprises additional material selectively located on a top of the one or more windings of the continuous conduit to enhance conformance and consistency of the cap system to the body part.

9. The hypothermia system according to claim 8, wherein the continuous conduit is routed through a larger stiffer conduit with an end portion fastened to the conformal cap system and an opposite end portion extending toward the inlet and outlet connectors.

10. The hypothermia system according to claim 1, further comprising one or more tie downs connected to the outer shell and strap of the conformal cap system to wrap around the user's arms or torso to further aid in a snug fit of the cap to the body part.

* * * * *